United States Patent
Derkx

(10) Patent No.: US 10,758,164 B2
(45) Date of Patent: Sep. 1, 2020

(54) PROCESSING APPARATUS AND PROCESSING METHOD FOR DETERMINING A RESPIRATORY SIGNAL OF A SUBJECT

(71) Applicant: KONINKLIJKE PHILIPS N.V., Eindhoven (NL)

(72) Inventor: Rene Martinus Maria Derkx, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 319 days.

(21) Appl. No.: 14/910,843

(22) PCT Filed: Aug. 1, 2014

(86) PCT No.: PCT/EP2014/066588
§ 371 (c)(1),
(2) Date: Feb. 8, 2016

(87) PCT Pub. No.: WO2015/018752
PCT Pub. Date: Feb. 12, 2015

(65) Prior Publication Data
US 2016/0183846 A1  Jun. 30, 2016

(30) Foreign Application Priority Data
Aug. 9, 2013 (EP) .................................. 13179939

(51) Int. Cl.
*A61B 5/08* (2006.01)
*A61B 5/113* (2006.01)
(Continued)

(52) U.S. Cl.
CPC ............ *A61B 5/113* (2013.01); *A61B 5/0816* (2013.01); *A61B 5/1121* (2013.01);
(Continued)

(58) Field of Classification Search
CPC .................. A61B 5/113; A61B 5/7246; A61B 2562/0219; A61B 5/6833; A61B 5/1121;
(Continued)

(56) References Cited

U.S. PATENT DOCUMENTS 6,064,910 A    5/2000 Andersson et al.
2009/0131809 A1 5/2009 Huang et al.
(Continued)

FOREIGN PATENT DOCUMENTS

CN    101209205 A   7/2008
CN    202168825 U   3/2012
(Continued)

OTHER PUBLICATIONS

Liu, G-Z et al., "Estimation of respiration rate from three-dimensional acceleration data based on body sensor network", Telemedicine Journal and E-Health, Nov. 2011: 17(9), 705-711.
(Continued)

*Primary Examiner* — Navin Natnithithadha
*Assistant Examiner* — Andrey Shostak

(57) ABSTRACT

A processing apparatus (6) for determining a respiration signal (34) of a subject (100) is presented. The processing apparatus (6) is configured to perform the steps of obtaining a movement signal (22) descriptive of a respiratory movement, determining a first quantity (24) descriptive of a rotation axis and/or rotation angle based on the obtained movement signal (22), and estimating a rotation axis (25) and/or rotation angle (26) based on the first quantity (24) and a rotation model, wherein the rotation model models the respiratory movement as a rotation around a single rotation axis. This model of the rotation can be further used as a feature for an instantaneous classifier descriptive of a movement artifact descriptive of a non-respiratory movement. Furthermore, a processing method, a respiration monitor (1,
(Continued)

91), a computer-readable non-transitory storage medium and a computer program are presented.

9 Claims, 6 Drawing Sheets

(51) Int. Cl.
*A61B 5/00* (2006.01)
*A61B 5/11* (2006.01)

(52) U.S. Cl.
CPC .......... *A61B 5/1135* (2013.01); *A61B 5/6833* (2013.01); *A61B 5/7207* (2013.01); *A61B 5/7246* (2013.01); *A61B 5/7264* (2013.01); *A61B 5/7225* (2013.01); *A61B 2562/0219* (2013.01)

(58) Field of Classification Search
CPC ... A61B 5/0816; A61B 5/7264; A61B 5/7207; A61B 5/1135; A61B 5/7225
See application file for complete search history.

(56) References Cited

U.S. PATENT DOCUMENTS

| | | |
|---|---|---|
| 2010/0286545 A1 | 11/2010 | Wolfe et al. |
| 2011/0021928 A1 | 1/2011 | Giovangrandi et al. |
| 2011/0066008 A1 | 3/2011 | Banet et al. |
| 2011/0066041 A1 | 3/2011 | Pandia et al. |
| 2012/0029375 A1 | 2/2012 | Lane et al. |
| 2012/0172681 A1 | 7/2012 | Sun et al. |
| 2012/0296221 A1 | 11/2012 | Morren |
| 2012/0302900 A1 | 11/2012 | Yin et al. |
| 2014/0158124 A1* | 6/2014 | L'her ................. A61B 5/0205 128/203.14 |

FOREIGN PATENT DOCUMENTS

| | | | |
|---|---|---|---|
| EP | 2263532 A1 | 12/2010 | |
| GB | 2493362 A | 2/2013 | |
| JP | 2012528657 A | 11/2012 | |
| WO | 03005893 A2 | 1/2003 | |
| WO | 2011133582 A1 | 10/2011 | |
| WO | 2011151634 A1 | 12/2011 | |
| WO | WO 2011151634 A1 * | 12/2011 | ........... A61B 5/0816 |
| WO | 2012095813 A1 | 7/2012 | |
| WO | 2013106700 A1 | 7/2013 | |

OTHER PUBLICATIONS

Hung, P.D. et al., "Estimation of respiratory waveform using an accelerometer", Biomedical Imaging: From Nano to Macro, 2008, 5th IEEE International Symposium, May 14-17, 2008, pp. 1493-1496.

Yin, B. et al., "Performance evaluation of a tri-axial accelerometry-based respiration monitoring for ambient assisted living", Engineering in Medicine and Biology Society, 2009, Annual International Conference of the IEEE, Sep. 3-6, 2009, pp. 5677-5680.

Gavriely, N., "Breath Sounds Methodology", CRC Press, 1995, ISBN 0-8493-5500-1.

Bates, A. et al, "Respiratory rate and flow waveform estimation from tri-axial accelerometer data," International Conference on Body Sensor Networks, Abstract.

* cited by examiner

PROCESSING APPARATUS AND PROCESSING METHOD FOR DETERMINING A RESPIRATORY SIGNAL OF A SUBJECT This application is a national stage application under 35 U.S.C. § 371 of International Application No. PCT/EP2014/066588 filed on Aug. 1, 2014 and published in the English language on Feb. 12, 2015 as International Publication No. WO 2015/018752 A1, which claims priority to EP Application No. 13179939.7 filed on Aug. 9, 2013, the entire disclosures of which are incorporated herein by reference.

FIELD OF THE INVENTION

The present invention relates to a processing apparatus and processing method for determining a respiratory signal of a subject.

BACKGROUND OF THE INVENTION

The respiratory rate has proven to be a good indicator of the deterioration of the condition of a patient. In combination with other vital signs, the respiratory rate plays a crucial role in early warning systems. Therefore, there is a need for continuous and reliable monitoring of a respiration signal, from which the respiratory rate is extracted, in intensive care units of hospitals. A similar need is present in the general ward setting of hospitals and in home healthcare applications, such as in telemedicine and chronic disease management.

While continuous monitoring of the respiration signal is available on bed side monitors for intensive care patients, various portable sensor systems are being developed to allow unobtrusive and prolonged measurement and monitoring of the respiration signal of mobile patients in general wards and in home healthcare settings with minimal discomfort.

Respiration monitoring can be based on different principles: the measurement of respiratory effort, for example thorax impedance plethysmography, respiratory inductance plethysmography, accelerometers, photoplethysmography or the measurement of respiratory effect, for example sound recording, temperature sensing, carbon dioxide sensing. Some sensors are already well established to monitor respiration. In intensive care units for example, thorax impedance plethysmography is the method of choice, whereas in sleep studies respiratory inductance plethysmography, often referred to as respiration band or respiband, is also commonly used. For ambulatory patients, such as on the general ward or in home healthcare, these sensors have limitations. A respiration band, for example, is considered to be too obtrusive and cumbersome by both medical personnel and patients.

A respiration monitoring system based on a multi-axial accelerometer overcomes these disadvantages. A multi-axial accelerometer is a device that measures an acceleration in multiple sensing axes. By evaluating the acceleration due to gravity with the different sensing axes, an accelerometer can be used as an inclinometer. The accelerometer is applied to an abdomen or a chest of a subject. The measured time-varying inclination reflects the abdomen or chest movement caused by respiration. This technique requires reliable signal processing to enable reliable monitoring under different conditions and postures of the patient.

Motion artifact is a well-known problem in patient monitoring. A motion artifact refers to a contamination of a physiological signal and a degradation of the measurement quality caused by physical activities of a patient, such as posture change, movement and talking Motion artifacts are more pronounced in a general ward setting than in an intensive care unit setting, since patients in the general ward setting generally have a more mobile activity pattern and are monitored most of the time without constant nursing surveillance, thus lacking knowledge on the presence of the physical activities and the measurement context. The problem becomes even more severe when monitoring patients in home healthcare settings.

Thus, if a multi-axial accelerometer is used to measure the respiratory rate in ambulatory conditions, such as home healthcare or a general ward, the accelerometer signals do not only change due to the respiration of a person but the accelerometer signals are also affected by unwanted motions that are not caused by respiratory motions.

Motion artifacts with frequency components that are different from breathing frequencies can be suppressed by straight-forward filtering in the frequency-domain. However, some of these unwanted motions, which may have a frequency component in the same range as the respiration, i.e., 0.1 Hz to 2 Hz or 6 respirations per minute to 120 respirations per minute, cannot be suppressed with a filter with a fixed frequency response.

US 2012/0296221 A1 discloses a method and apparatus for determining a respiration signal using an accelerometer. A vector magnitude of the accelerometer signals is evaluated to identify any unwanted or non-respiratory motion contributions to the acceleration signals. For a static, i.e. non-moving, multi-axial accelerometer the vector magnitude is always the same irrespective of the orientation of the sensor. If the position of the center-point of the tri-axial accelerometer changes due to whole body movements, for example walking, however, this causes an additional inertial acceleration component in addition to the acceleration due to gravity. A non-respiratory, inertial motion contribution is identified and then used to suppress and adaptively filter this unwanted motion contribution from at least one of the accelerometer signals. From the at least one filtered accelerometer signal, a respiration signal is determined that reliably and accurately represents the respiration of the subject.

US 2011/0066041 A1 discloses a respiration monitoring device including an accelerometer for application to the chest, whereby acceleration is possible due to both non-respiratory body motion and respiration, and an electronic circuit responsive to an acceleration signal from the accelerometer and operable to separate from the acceleration signal a heart signal, a respiration signal, and a substantially non-respiration body motion signal.

US 2011/0021928 A1 discloses noninvasive methods and systems of determining and monitoring an individual's respiration pattern, respiration rate, other cardio-respiratory parameters or variations thereof. In an embodiment, a single, miniature and chest-worn accelerometer is utilized to capture respiration-dependent parameters.

WO 2013/106700 A1 discloses systems and methods for determining mental and physical health using multi-scale metrics.

SUMMARY OF THE INVENTION

It is an object of the present invention to provide an alternative processing apparatus and processing method which reliably determines a respiration signal. Advantageously, the determination of the respiration signal involves a limited computational effort for low power consumption and provides a quick initial reading of the respiration signal, for example, after attaching the device on a patient or after a movement artifact has occurred.

In a first aspect of the present invention a processing apparatus for determining a respiration signal of a subject is presented that is configured to perform the steps of obtaining a movement signal descriptive of a respiratory movement, determining a first quantity descriptive of a rotation axis and/or rotation angle based on the obtained movement signal, and estimating a rotation axis and/or rotation angle based on the first quantity and a rotation model, wherein the rotation model models the respiratory movement as a rotation around a single rotation axis.

In another aspect of the present invention, a processing method for determining a respiration signal of a subject is presented that comprises the steps of obtaining a movement signal descriptive of a respiratory movement, determining a first quantity descriptive of a rotation axis and/or rotation angle based on the obtained movement signal, and estimating a rotation axis and/or rotation angle based on the first quantity and a rotation model, wherein the rotation model models the respiratory movement as a rotation around a single rotation axis.

In another aspect of the present invention, a respiration monitor for measuring a respiration signal of a subject is presented that comprises a sensor for measuring a movement signal descriptive of a respiratory movement, and the aforementioned processing apparatus for determining a respiration signal of a subject.

In yet further aspects of the present invention, there are provided a computer program which comprises program code means for causing a computer to perform the steps of the method disclosed herein when said computer program is carried out on a computer as well as an non-transitory computer-readable recording medium that stores therein a computer program product, which, when executed by a processor, causes the method disclosed herein to be performed.

Preferred embodiments of the invention are defined in the dependent claims. It shall be understood that the claimed processing method, respiration monitor, computer program and recording medium have similar and/or identical preferred embodiments as the claimed processing apparatus and as defined in the dependent claims.

With the processing apparatus according to an aspect of the present invention, a respiration signal of a subject can be determined in reliable and computationally efficient way. The inventors have found that, as an alternative to identifying unwanted motion contributions by evaluating an inertial acceleration component in addition to the acceleration due to gravity, identifying a non-respiratory motion contribution therefrom, and then performing adaptive filtering for filtering out the unwanted motion contributions, it is possible to estimate a rotation axis and/or rotation angle based on a rotation model, wherein the rotation model models the respiratory movement as a rotation around a single rotation axis. The respiratory movement can be described by a rotatory movement around a single rotation axis with small rotation angles. Studies of the inventors have shown that the rotations can be typically described as micro-rotations up to ±1 or 2 degrees.

The term 'movement signal' as used herein relates to a signal descriptive of a respiratory movement. Such a movement signal can be acquired using a multi-axial accelerometer, in particular, a commercially available tri-axial accelerometer such as for example the Bosch BMA355, ST Microelectronics LIS3DSH or ST Microelectronics LIS344ALH. Alternatively, a multi-axial gyroscope can be used to acquire movement data, such as for example the ST Microelectronics LYPR540AH. However, the use of an accelerometer is preferred since accelerometers typically feature a lower power consumption compared to gyroscopes and are available at lower cost. A low power consumption is especially important for a battery-powered respiration monitor.

The 'first quantity' descriptive of a rotation axis and/or rotation angle is determined based on the obtained movement signal. For example, the tri-axial accelerometer can be used as inclinometer to reflect a respiratory abdomen or chest movement caused by respiration based on the fact that the magnitude of the inertial acceleration caused by a respiratory movement is relatively small compared to the change of gravitational components due to a rotatory component of the respiratory movement.

A tri-axial accelerometer is a device that measures the acceleration in three, typically orthogonal, directions referred to as sensing axes x, y, and z. Thereby, the direction of the gravitational force with respect to the accelerometer can be determined. A respiratory movement and thus a movement of the acceleration sensor, affects the orientation of the gravitational force with respect to an orientation of the sensor. This is also referred to as the movement signal. For example, a reading of a sensor comprises a three element vector having an x-, y-, and z-component representing the acceleration measured on the respective sensing axes. The movement signal can represent a series of such vectors over time.

The first quantity descriptive of a rotation axis and/or rotation angle can be calculated from the movement signal by evaluating the measured values. The first quantity thus represents the measured rotation axis and/or measured rotation angle. For example, the rotation axis and rotation angle can be determined by comparing a measured vector with a previous or average vector. In practical applications, the movement signal is not a perfect signal only containing contributions from a respiratory movement but also noise and motion artifacts. According to an aspect of the present invention, the determination of the respiratory signal does not rely on the first quantity only, but uses the first quantity in combination with a rotation model for estimating a single rotation axis and/or rotation angle. The rotation model can be thought of as an anticipated respiratory movement around a single rotation axis and optionally also takes into account that anticipated respiratory movements are confined to small angular rotations. In other words, the estimated rotation axis and/or estimated rotation angle represent a portion of the first quantity, thus a portion of the measured rotation axis and/or measured rotation angle that corresponds to an anticipated respiratory movement described by the rotation model. Alternatively, the estimation of rotation axis and/or rotation angle can be thought of as a projection of the measured first quantity onto a modeled value.

In a preferred embodiment, the processing apparatus is further configured to perform the step of determining an instantaneous classifier descriptive of a movement artifact descriptive of a non-respiratory movement. Essentially, the instantaneous classifier represents a mismatch between the obtained movement signal or first quantity and a value that is expected based on the estimated rotation axis and/or rotation angle from the rotation model. Advantageously, the processing apparatus is configured for determining the instantaneous classifier on a sample-by-sample basis. Alternatively, to reduce the amount of calculations, several samples can be grouped as blocks such that the analysis is performed on blocks instead of individual samples.

An advantage of the instantaneous classifier is that movement artifacts can be determined with low latency. Some previous algorithms rely on the determination of spectral features and filtering in the frequency domain. This involves extensive calculations for Fourier transforms and the like. Furthermore, sufficiently long signal traces for meaningful frequency analysis have to be acquired, which leads to a latency. An approach that performs filtering, frequency analysis or evaluates spectral features such as entropy and periodicity typically requires the processing of longer time windows, for example a 30 second long time window, to determine deviations due to motion artifacts. The processing apparatus according to this embodiment of the invention provides a quick initial response with low latency and is able to detect and reject movement artifacts on a small timescale.

For example, a nurse wants to see a quick initial response to decide whether a respiration sensor is attached properly or not. Optionally a respiratory waveform, as a graphical representation of the respiration signal, is presented in combination with the instantaneous classifier. Optionally a quick initial respiratory rate estimation is provided.

Furthermore, a classification of spectral features of time windows according to the prior art could lead to a classification of the whole time windows as being bad even when there a relatively small-duration movement artifacts. Hence, the coverage, i.e., the amount of time for which a valid respiration signal can be measured, deteriorates. An instantaneous classifier can thus help to improve the coverage of a meaningful respiration signal.

In a further embodiment, the step of determining the first quantity comprises the step of comparing the obtained movement signal with an averaged movement signal. For example a rotation of a currently acquired value of the movement signal can be compared with or evaluated against an average value of the movement signal. Thereby, a rotation angle and/or rotation axis compared to the average movement signal can be determined.

Advantageously, the step of comparing the obtained movement signal with the averaged movement signal comprises computing a cross product of a vector descriptive of the movement signal and an average vector descriptive of the averaged movement signal. In case of a gyroscope, the step of comparing the obtained movement signal with the averaged movement signal comprises a difference computation of the vector descriptive of the movement signal and an averaged vector descriptive of the average movement signal. Optionally, the average vector can be a moving average and/or a weighted average of vectors descriptive of the movement signal. An example for weighted averaging is exponential averaging. The comparison of a currently measured vector with an average value is advantageous, because the impact of noise is reduced compared to comparing two successive vectors.

In a further refinement, the processing apparatus is further configured for adapting the averaging to a stability of the respiratory movement. For example, the duration of averaging can be adapted. For example, the averaging accounts for a posture change in that only values are taken into account wherein the posture has not changed significantly. A posture change in turn can be indicated by the instantaneous classifier descriptive of a movement artifact.

In a further embodiment, the step of estimating the rotation axis and/or rotation angle based on the rotation model comprises the step of performing a principal component analysis of the first quantity. Thereby, the first principal component analysis gives a predominant rotation axis that can be used as the estimated rotation axis. The estimated rotation axis can be represented by a vector or normalized vector. Alternatively, the estimated rotation axis is calculated as an average of the first quantity descriptive of a rotation axis.

In a further refinement, the rotation angle is estimated based on a projection of the first quantity onto the estimated rotation axis. For example, the first quantity is calculated as the cross product of a vector descriptive of the movement signal and an average vector descriptive of the average movement signal. By projecting first quantity, that potentially comprises noise and motion artifacts, onto the estimated rotation axis, only those contributions of the movement signal are extracted that lie within the predetermined rotation axis that is anticipated for the respiratory movement. Thereby, unwanted contributions can be effectively eliminated. No extensive filtering in the frequency-domain is required. As a computational efficient implementation, the projection of the first quantity onto the estimated rotation axis can be calculated by taking the scalar or dot product of the first quantity and the estimated rotation axis.

In a further embodiment, the instantaneous classifier is descriptive of a mismatch between the movement signal and an estimated movement signal from the rotation model. The movement signal represents the obtained movement signal descriptive of the respiratory movement. The estimated or expected movement signal represents an expected value that is anticipated for the obtained movement signal by the respiration model for a respiratory movement as a rotation around a single rotation axis. For example, the obtained movement signal is a vector comprising the x-, y- and z-components acquired with a tri-axial accelerometer. The estimated movement signal is in example equals the measured x-, y- and z-components, if the measured movement signal actually were a purely rotational movement around a single rotation axis. Of course, an evaluation of a mathematical equivalent representation of the movement signal and the estimated movement signal is within the scope of this embodiment.

In a further refinement, the processing apparatus is further configured to compute a difference between the obtained movement signal and the estimated movement signal. A difference between the two vectors is computed as a feature-value for the instantaneous classifier to detect movement artifacts. For example, the instantaneous classifier indicates if the difference exceeds a threshold. Alternatively, the instantaneous classifier indicates if a variance of the difference exceeds a threshold.

In another embodiment, the processing apparatus is further configured to compute a quality index. The quality index represents an average or smoothened feature-value that was also used in the instantaneous classifier. For example, the quality index can be an easy-to-understand figure from 0 to 1 or from 0% to 100%.

In yet another embodiment, the processing apparatus is further configured to perform the step of recovering a respiratory phase of the respiratory movement. The basic respiratory phases are inhalation and exhalation. It is necessary to recover the respiratory phase because a sensor for acquiring the movement signal can be applied to the body of the subject in different orientations, such that a movement in one direction cannot be unambiguously attributed to a particular respiratory phase, for example an inhalation. An advantage of recovering the respiratory phase is that the sensor can be placed on the subject without taking care of the orientation of the sensor. The recovery of the respiratory waveform can involve evaluating the estimated angle over time, i.e. analyzing a waveform of the estimated angle over time and extracting phases of inhalation and exhalation therefrom.

In a refinement, the step of recovering the respiratory phase comprises determining the number of local extrema of a waveform descriptive of the estimated rotation angle and determining a baseline level of the waveform, and flipping the waveform when the number of extrema above the baseline level exceeds the number of extrema below the baseline level. The baseline level can be, for example, a zero-level or could also be determined via smoothing of the rotation angle, in particular with a long time-constant (e.g. 20 seconds). The baseline can be an average value of estimated rotation angles. The inventors have found that this analysis provides a reliable, yet easy to implement, measure for determining inhalation and exhalation. As a result, a respiratory waveform can be displayed with the same orientation regardless of the orientation of the sensor.

In a further embodiment, the sensor of the respiration monitor is one of a multi-axial accelerometer, a multi-axial gyroscope, and a combination of accelerometer and gyroscope. For example, a MEMS accelerometer can be used as an inexpensive device. Preferably, only one tri-axial accelerometer is used. Alternatively a combination of single-axis accelerometers is used that are arranged to cover different spatial axis. In an further embodiment, the sensor of the respiration monitor comprises a tri-axial gyroscope or alternatively a combination of single-axis gyroscopes. Further alternatively a combination of a single- or multi-axial accelerometer and a single- or multi-axial gyroscope can be employed.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
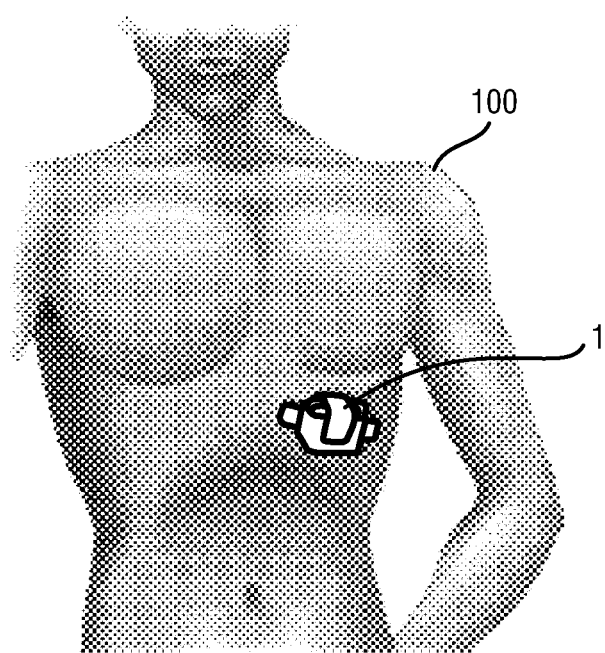
FIG. 1 shows an embodiment of a respiration monitor attached to a body of a subject.

FIG. 1 shows an embodiment of a respiration monitor 1 for measuring a respiration signal of a subject 100. The respiration monitor 1 is applied to a suitable location on the body of the subject 100 for measuring a respiratory movement. Suitable locations include but are not limited to the chest and rib-cage region, as depicted in FIG. 1. However, any part of the subject 100 that is affected by a respiratory movement, in particular the upper torso, can be envisaged.

The respiration monitor 1 according to an aspect of the present invention enables an unobtrusive measurement of the respiratory signal. As can be seen in FIG. 1, the respiration monitor 1 can be implemented as a small device that can simply be applied to the body of the subject 100. Conventional respiration monitoring devices, for example a nasal cannula are inconvenient for the patient. Alternative conventional respiration monitoring devices, such as for respiratory inductance plethysmography require more effort in handling. For respiratory inductance plethysmography (RIP) one or two RIP-bands have to be wrapped around the chest and/or abdomen of the subject 100. Especially for a heavy patient, the application of these bands can be cumbersome for a nurse. Nonetheless, respiratory inductance plethysmography is one of the most common techniques used for determining a respiration signal today. Further alternative conventional respiration monitoring devices include devices for thorax impedance plethysmography that are used in intensive care units. In thorax impedance plethysmography, the impedance is measured via two ECG electrodes, which is also inconvenient for the patient.

Figure 2:
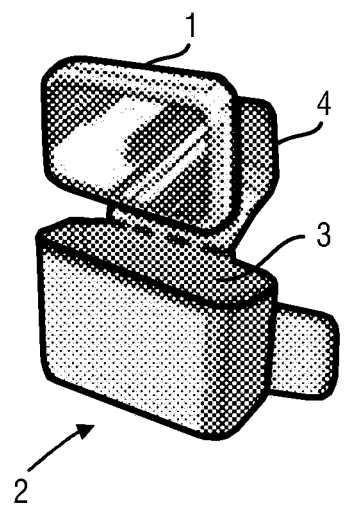
FIG. 2 shows a perspective view of the embodiment of the respiration monitor.

FIG. 2 shows the respiration monitor 1 and an application pocket 2. The application pocket 2 can be a disposable item that is applied to the skin of the subject 100. The application pocket 2 comprises a compartment 3 for receiving the respiration monitor 1 and a cover or lid 4 for closing and fixing the respiration monitor 1 in the compartment 3. Applying the respiration monitor 1 to the skin of the subject 100 includes, but is not limited to this embodiment. For example, the respiration monitor 1 can simply be taped to the skin of the subject 100. Alternatively, the respiration monitor 1 can also be attached to clothing of the subject 100, as long as the respiration monitor follows the respiratory movement. For example, the respiration monitor 1 can be seated in a pocket of a tight shirt.

Figure 3:
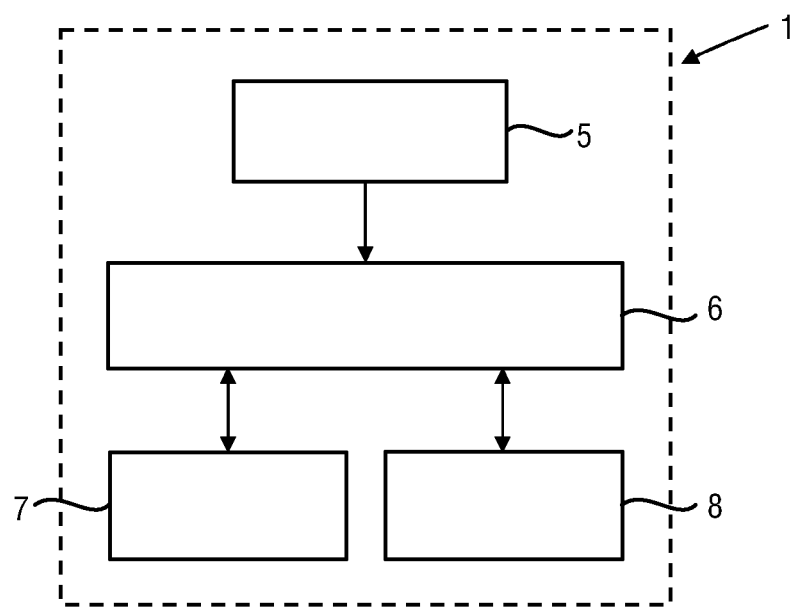
FIG. 3 shows a schematic diagram of an embodiment a respiration monitor.

FIG. 3 shows a block diagram of an exemplary embodiment of the respiration monitor 1 for measuring a respiration signal of the subject 100.

The respiration monitor 1 comprises a sensor 5 for measuring a movement signal descriptive of a respiratory movement and a processing apparatus 6 for determining a respiration signal. In this exemplary embodiment, the respiration monitor 1 further comprises an interface 7 and a memory 8.

The sensor 5 may, for example, comprise a multi-axial accelerometer which is adapted to generate a movement signal indicative of the acceleration along different spatial axes. In this embodiment, the multi-axial accelerometer is a tri-axial accelerometer adapted to generate a movement signal that comprises three accelerometer signals indicative of the acceleration along three orthogonal spatial axes. For example, three-axial accelerometers named Bosch BMA355, ST Microelectronics LIS3DSH, ST Microelectronics LIS344 ALH or Kionix KXM52 can be used. However, also other kinds of multi-axial accelerometers can be used for generating accelerometer signal indicative of the acceleration along different spatial axis. Furthermore, the sensor 5 may, for example, comprise a multi-axial gyroscope which is adapted to generate a movement signal indicative of the angular rotation along different spatial axes. For example, the ST Microelectronics LYPR540AH can be used to acquire angular rates for three orthogonal axes from which angular angles can be easily derived.

The movement signal is provided to the processing unit 6 for determining the respiration signal of the subject. The processing apparatus 6 is configured to perform the steps shown in the flow chart of FIG. 4 as described further below.

The interface 7 can be a wired or wireless interface for providing the respiration signal of the subject. Advantageously, the respiration monitor 1 is a battery-powered device and the interface 7 is wireless interface such that no cables are required. For example, the interface 7 can provide the respiration signal to a patient monitor for displaying a respiratory waveform on a screen. Alternatively, the interface 7 can be a human machine interface (HMI) for showing the respiration signal or any quantity derived thereof, such as for example the respiratory rate on a display of the respiration monitor 1.

The memory 8 can store the respiration signal that has been determined by the processing apparatus 6. Alternatively, the memory 8 can be a non-transitory storage medium containing instructions for execution by the processing apparatus, wherein the instructions cause the processing apparatus 6 to perform the steps of the flow chart shown in FIG. 4 or FIG. 6. For the case that the memory 8 stores the determined respiration signal, the respiration signal can be, for example, recorded over a period of time, such that no connection to an external entity such as patient monitor is required. The respiration signal can be downloaded after a desired measurement period. Thereby, the power consumption can be further reduced since no communication, in particular no wireless communication is required.

In an alternative embodiment, the sensor 5 and the processing apparatus 6 are not implemented in one device. For example, a minimum configuration of sensor 5 and interface 7 can be implemented as a device that is worn by the patient. Sensor signals are thus transmitted via the interface 7 to the processing apparatus 6 at a remote location. For example, the processing apparatus 6 can be implemented as a part of a patient monitor or of a healthcare infrastructure such as a hospital IT system. In a further embodiment, a smartphone or a similar device serves as the processing apparatus 6 and is configured to perform the steps for determining the respiration signal.

Figure 4:
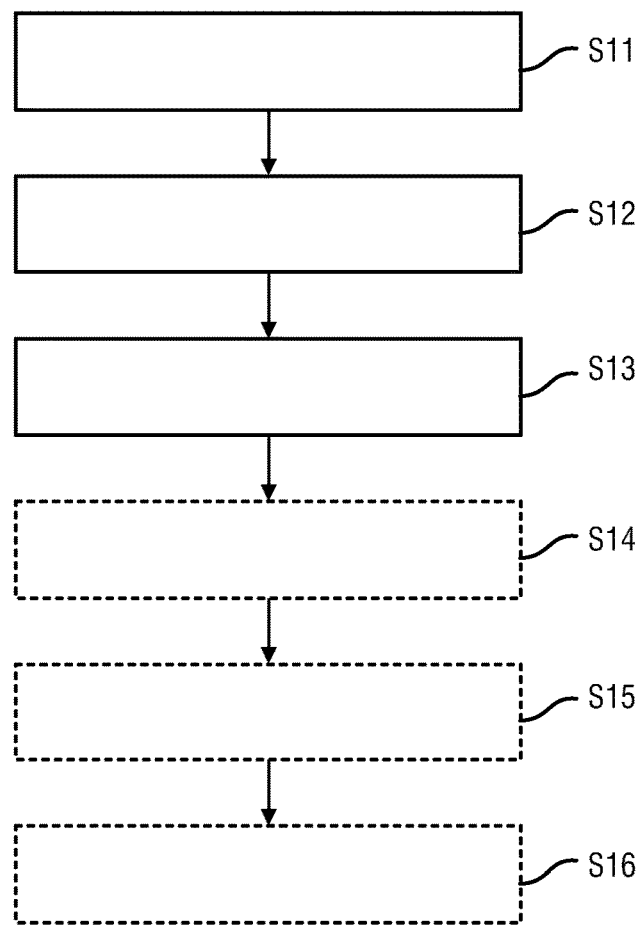
FIG. 4 shows a flow chart of an embodiment a processing method.
Figure 5:
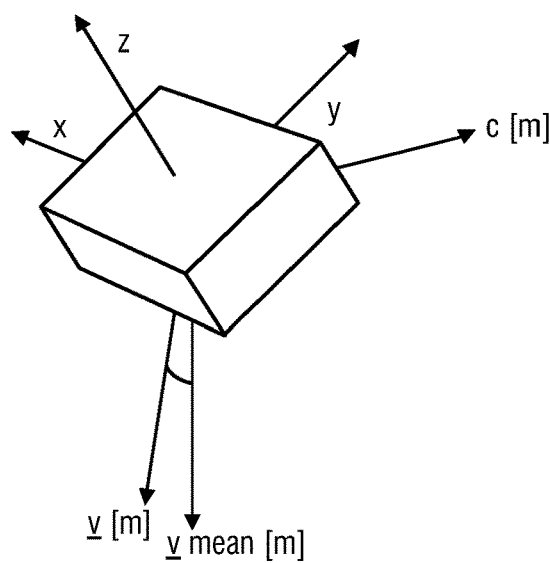
FIG. 5 shows a schematic diagram of a tri-axial accelerometer.

FIG. 4 shows a flow chart of the steps performed by the processing apparatus 6 according to an aspect of the present invention. In a first step S11 a movement signal descriptive of a respiratory movement is obtained. In a preferred embodiment, the movement signal is a series of vectors, wherein each vector comprises the x-, y- and z-components of a tri-axial accelerometer. A tri-axial accelerometer 5 is shown in FIG. 5 to illustrate the respective axis. In a second step S12, a first quantity descriptive of a rotation axis and/or a rotation angle is determined based on the obtained movement signal. For example, the obtained movement signal is compared with an average movement signal. Thereby, a rotation axis and/or rotation angle of a current orientation of the tri-axial accelerometer with respect to an average orientation of the tri-axial accelerometer can be determined. In a third step S13 a rotation axis and/or rotation angle is estimated based on the first quantity and a rotation model, wherein the rotation model models the respiratory movement as a rotation around a single rotation axis.

In an optional further step S14, an instantaneous classifier descriptive of a movement artifact descriptive of a non-respiratory movement is determined. Essentially, the instantaneous classifier evaluates a mismatch between the determined first quantity and a estimated rotation axis and/or rotation angle of the rotation model. Thereby, the actually obtained movement signal is compared to an anticipated respiratory movement which is described by the rotation model.

In an optional fifth step S15, a respiratory phase of the respiratory movement is recovered. In other words, a phase of inhalation and a phase of exhalation are identified in the respiration signal.

In an optional sixth step S16, the processing apparatus determines a respiratory rate from the respiration signal. The respiration signal can be thought of as a respiration waveform that displays inhalation and exhalation over time. The respiratory rate can be determined, for example, by means of a Fourier transform that transforms the time series into a frequency spectrum. However, advantageously for low latency and a quick display of the respiratory rate, the temporal separation of waveform features, such a temporal peak-to-peak separation can be evaluated. Optionally, an average value of waveform features is displayed. A duration of the averaging can be adapted based on a variation of the temporal separation of the waveform features to enable a quick response to a changing respiratory rate. However, the determination of the respiratory rate can alternatively also be performed by a further device such as a patient monitor.

The sequence of the steps of the flow chart in FIG. 4 can be altered. For example, the sequence of steps S14 and S15 can be switched. Alternatively, steps S14 and S15 can be carried out in parallel. Furthermore, the instantaneous classifier of step S14 can determine a condition for the determination of the respiratory rate S16. For example, the respiratory rate is only determined if the instantaneous classifier indicates a good quality of the respiratory signal, i.e., a signal that does not suffer from motion artifacts.

FIG. 5 shows a schematic diagram of a tri-axial accelerometer as the sensor 5. The components denoted by x, y, z are the orthogonal sensing axes of the accelerometer. The movement signal v descriptive of the respiratory movement comprises a series of vectors $\underline{v}[m]$ comprising the x-, y-, and z-components of the tri-axial accelerometer. The quantity $\underline{v}[m]$ denotes a measured vector, wherein m is a time-discrete index. The quantity $\underline{v}_m[m]$ denotes an averaged vector descriptive of an averaged measured movement signal. The quantity $\underline{c}[m]$ denotes the first quantity descriptive of a rotation axis and/or rotation angle based on the obtained movement signal $\underline{v}$. In the following, underlined quantities with an index, e.g. [m], refer to a vector, underlined quantities without index refer to a series of vectors that represent a signal over time, and a non-underlined quantities refer to scalars.

Assuming that the rotation of the sensor occurs around a single axis, the first quantity $\underline{c}[m]$ can be computed by the cross product $$\underline{c}[m] = \underline{v}[m] \times \underline{v}_{mean}[m]. \tag{1}$$

The magnitude of the cross product can be interpreted as the area of the parallelogram having $\underline{v}[m]$ and $\underline{v}_{mean}[m]$ as sides $$\|\underline{c}[m]\| = \|\underline{v}[m]\| \cdot \|\underline{v}_{mean}[m]\| \cdot |\sin(\phi[m])|, \tag{2}$$

where ϕ[m] is related to the angle between the two vectors.

For the vector $\underline{v}_{mean}[m]$, an average over time of vectors $\underline{v}[m]$ is computed. For example an average of the past K vectors $\underline{v}[m]$ is computed by $$\underline{v}_{mean}[m] = \frac{1}{K+1} \sum_{i=m-K}^{m} \underline{v}[i], \tag{3}$$

where K is taken sufficiently large to cover at least a single breath. If the breathing is stable, the value of K can be extended over multiple breaths.

As an alternative to averaging with a rectangular window having equal weights over the past input vectors, a weighted averaging can be applied. For example, exponential averaging with a memory of several seconds can be applied, i.e., $$\underline{v}_{mean}[m]=\beta \underline{v}_{mean}[m-1]+(1-\beta)\underline{v}[m], \quad (4)$$

where β is the recursive averaging value computed as $$\beta = \exp\left(-\frac{1}{T_{avg}F_S}\right), \quad (5)$$

where $F_s$[Hz] is a sampling rate and $T_{avg}$[s] is a averaging time. Exemplary values are $T_{avg}$=4 seconds and $F_s$=15.625 Hz, giving a value of β=0.984.

Figure 6:
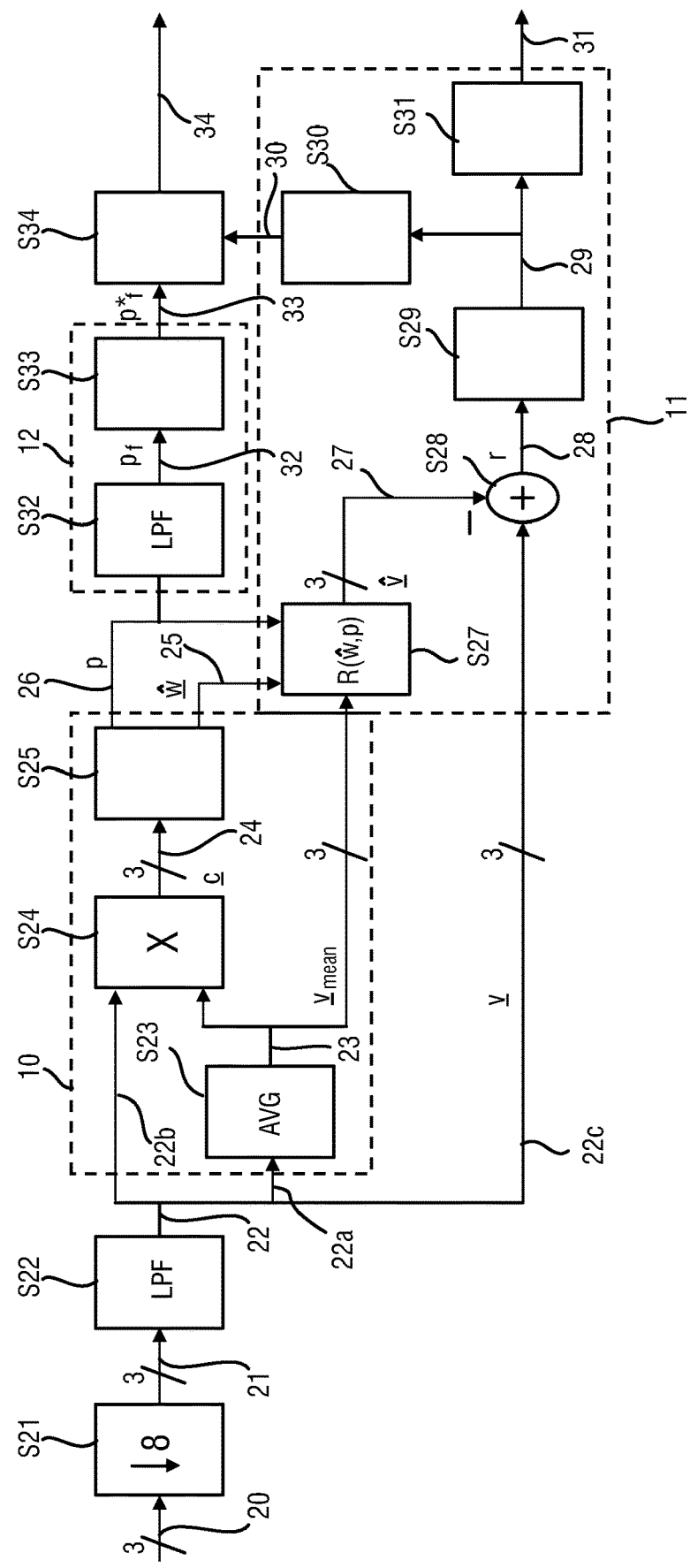
FIG. 6 shows a detailed flow chart of the steps performed by an embodiment the proposed processing apparatus.

FIG. 6 shows a flow chart of an exemplary signal flow performed by an embodiment of the processing apparatus according to an aspect of the present invention. The steps performed by the processing apparatus can be grouped into three interdependent functional blocks: rotation model 10, instantaneous classifier 11 and phase recovery 12.

1. Rotation Model

As shown in FIG. 6, the functional blocks can be preceded by optional preprocessing steps performed on an output signal of the sensor 5. The processing apparatus 6 obtains a raw movement signal 20 descriptive of the respiratory movement of the subject in the form of a series of three element vectors. The three elements represent the x-, y-, and z-components of a tri-axial accelerometer. In this embodiment, the raw movement signal 20 is obtained with a sample rate of 125 Hz. In an optional step S21, the obtained signal 20 is downsampled by a factor 8. Thereby, the sampling rate is reduced to 15.625 Hz. Thus an average value of eight samples is forwarded as an intermediate movement signal 21 to step S22. An advantage of downsampling is that the computational effort can be reduced.

In the optional step S22 the signal is pre-filtered. A low pass filter (LPF), a band-pass filter for typical breathing frequencies or any other type of pre-filter can be used for conditioning the intermediate movement signal 21. Furthermore, the filter can be an adaptive filter or a filter with fixed frequency response. However a rather simple filter is preferred to reduce a computational effort and/or latency. Alternatively, no pre-filter is used.

The preprocessed movement signal 22 is split in three and now denoted as movement signal $\underline{v}$. The first branch 22a is used in step S23 to compute the average movement signal $\underline{v}_{mean}$ 23. The average movement signal $\underline{v}_{mean}$ comprises a series of vectors $\underline{v}_{mean}[m]$. Examples for calculating $\underline{v}_{mean}[m]$ are given in equations (3) and (4).

In step S24, the first quantity $\underline{c}$ 24 is computed 24 based on the average movement signal $\underline{v}_{mean}$ 23 and the second branch of the preprocessed movement signal $\underline{v}$ 22b as described in equation (1). In this embodiment, the first quantity can also be referred to as cross product signal comprising cross product vectors $\underline{c}[m]$.

In step S25, a principal component analysis is performed to determine the single rotation axis ŵ 25 and estimate the angle signal p 26. The estimated angle signal p 26 comprises a time series of the estimated angle p[m].

Intuitively, it can be understood that the norm of the cross product vector $\underline{c}[m]$ represents the angle of rotation of $\underline{v}[m]$ with respect to $\underline{v}_{mean}[m]$. This holds true under the assumption that $\|\underline{v}[m]\| \approx 1$ and $\|\underline{v}_{mean}\| \approx 1$. In other words, the cross-product vector $\underline{c}[m]$ has a direction that is perpendicular to $v[m]$ and $v_{mean}[m]$ with a length that is representative of the angle between $\underline{v}[m]$ and $\underline{v}_{mean}[m]$.

In practice, however, there can be fluctuations and noise on the movement signal $\underline{v}$, and the rotation can be non-ideal. Therefore, a principal component analysis method (PCA) can be applied in step S25 to the cross product signal $\underline{c}$ for determining the principal axis of rotation of the movement signal $\underline{v}$. Thus a series of vectors $\underline{c}[m]$ from equation (1) serve as an input for the principal component analysis (PCA). The rotation axis 25 that is identified by the PCA is denoted by ŵ.

Optionally, the rotation axis is also a series of rotation axis ŵ[m] that are computed repeatedly. Thus, the PCA is adaptive and tracks the rotation-axis ŵ[m] continuously. The speed of this adaptation can optionally be adjusted by a parameter that is chosen by a trade-off between accuracy and speed of convergence. Further optionally, alternative dimension reduction techniques can be used instead of PCA. Such techniques are also referred to as sub-space methods.

Based on the identified rotation axis ŵ[m] and the first quantity $\underline{c}[m]$, an estimated angle p[m] can be computed by the dot product or scalar product given by $$p[m]=\underline{c}[m]\cdot\underline{\hat{w}}[m] \approx \sin(\eta\phi[m]), \quad (6)$$

The quantity p[m] is thus a scalar value that represents the estimated rotation angle. It should be noted that equation (6) further comprises an attenuation factor η, wherein $$0<\eta\leq 1. \quad (7)$$

The introduction of the parameter η is a consequence of the fact that the sensor also can also subject to rotations around the gravity vector that cannot be measured by the sensor. This factor η is more close to 0 when the amount of rotation around the gravity vector increases. Another consequence of a rotation around the gravity vector is that the rotation axis (identified by the PCA) does not necessarily represent the physical rotation axis anymore, but only the contribution of a respiratory movement that does not coincide with the gravity vector.

The rotation angles due to a respiratory movement are typically in the order of ±1 or 2 degrees. Therefore, the quantity p[m] can be directly related to ηφ[m] without applying an arcsin operator. For simplicity, the quantity p[m] can be directly referred to as the estimated rotation angle. The time series of estimated rotation angles p[m] gives the estimated rotation angle signal 26 denoted by p.

In an embodiment, the signal p can be directly interpreted as the respiration signal of the subject without further processing. However, advantageously additional signal processing steps further improve a quality of the respiration signal by determining an instantaneous classifier 11 descriptive of a movement artifact of a non-respiratory movement and/or by recovering a respiratory phase 12.

2. Instantaneous Classifier

The determination of the instantaneous classifier in block 11 essentially is a check whether the rotation of the sensor fits the rotation model. If there is no small rotation around a single rotation axis this is indicated by the instantaneous classifier.

In the embodiment shown in FIG. 6, the first step S27 in the instantaneous classifier block 11 is to reconstruct the gravity-influenced part of the data $\hat{\underline{v}}[m]$. The vectors $\hat{\underline{v}}[m]$ constituting the estimated movement signal $\hat{\underline{v}}$ 27 are calculated based on the following equation:

$$\hat{\underline{v}}[m]=R(\hat{\underline{w}}, p)[m]\underline{v}_{mean}[m],$$

where the vector $\underline{v}_{mean}[m]$ is rotated around the axis defined by $\hat{\underline{w}}[m]$ by an angle of p[m]. The rotation matrix R ($\hat{\underline{w}}[m]$, p[m])≙ R($\hat{\underline{w}}$, p)[m] is defined as:

$$R(\hat{\underline{w}}, p)[m] = \begin{pmatrix} (a^2+b^2)-(b^2+c^2) & 2(-a\cdot d+b\cdot c) & 2(a\cdot c+b\cdot d) \\ 2(a\cdot d+b\cdot c) & (a^2+c^2)-(b^2+d^2) & 2(-a\cdot b+c\cdot d) \\ 2(-a\cdot c+b\cdot d) & 2(a\cdot b+c\cdot d) & (a^2+d^2)-(b^2+c^2) \end{pmatrix} \quad (9)$$

where the values of a, b, c and d are calculated for each new vector v[m] of the movement signal v and are given by a quaternion $\underline{q}_r[m]$. This quaternion is a unit vector: $\|\underline{q}_r[m]\|=1$ and is given by:

$$\underline{q}_r[m] = \begin{pmatrix} a \\ b \\ c \\ d \end{pmatrix} = \begin{pmatrix} \cos(p[m]/2) \\ \sin(p[m]/2)\hat{\underline{w}}[m] \end{pmatrix}. \quad (10)$$

In the next step S28, the residual model error r[m] is computed by:

$$\underline{r}[m] = \underline{v}[m] - \hat{\underline{v}}[m] \quad (11)$$

giving an error signal 28 denoted by r.

Ideally, when the rotation of the sensor perfectly fits the rotation model, the obtained movement signal corresponds to the estimated movement signal, thus $\hat{\underline{v}}[m]=\underline{v}[m]$ and $\underline{r}[m]$ will be equal to an all-zero vector. However, in practice, there are motion artifacts and other disturbances causing rotations that cannot be modeled by a rotation around a single fixed rotation axis ŵ. During a motion artifact, there are typically large rotations around multiple axis and the estimated rotation axis ŵ deviates from a rotation axis described by the first quantity c. Especially when the angular rotation becomes larger, the chances of deviations from the model will become bigger.

Furthermore, there can be model errors during the process, for example that weights of the PCA performed in step S25 have to (re)converge, e.g. after initially applying the sensor to the subject or after a posture change. Also in such case, the residual vector r[m] is or will become larger.

During a motion artifact, an adaptive PCA continues to adapt, although very slowly. However, the PCA does not converge to a stable rotation axis. After the motion artifact, the PCA is able to converge again to a correct rotation axis that is representative of the breathing-induced micro-rotations. Optionally, the processing apparatus speeds up the adaptation of the PCA for a small time-period after the movement artifact has occurred. This enables a faster convergence to the new stable rotation axis.

In a preferred embodiment, the variance of r is determined in step S29. As the variance of r[m] is a good indicator for movement artifacts or model errors, the variance of r[m] is proposed as a (single) feature for the instantaneous classifier. The variance is denoted by Var[m], the variance signal 29 is denoted by Var.

As an sub-step of step S29, a value descriptive of the residual model error r[m] can be determined. For example, the $L_2$ norm is computed on a sample-by-sample basis, $$L_2[m] = \|\underline{r}[m]\| \quad (12)$$

$$\overset{\Delta}{=} \sqrt{\sum_{c=0}^{2} (r[m])_c^2}$$

$$= \sqrt{r_x^2[m] + r_y^2[m] + r_z^2[m]}.$$

where c denotes the index of the vector elements, thus the x-, y-, and z-component.

In a next sub-step of step S29, the variations of $L_2[m]$ over time are computed. For example, the variance is computed over a block of B samples (e.g. B=16 samples equals roughly 1 second for a sampling rate of Fs=15.625 Hz):

$$\text{Var}[K_B B] = \sqrt{\frac{1}{B}\sum_{i=0}^{B-1}(L_2[K_B B + i] - \overline{L_2}[K_B B])^2}, \quad (13)$$

where $$\overline{L_2}[K_B B] = \frac{1}{B}\sum_{i=0}^{B-1} L_2[K_B B + i] \quad (14)$$

and $K_B=0, 1, \ldots, \infty$ is the block-index. In this example, the blocks are non-overlapping blocks of B samples. Alternatively, overlapping blocks can be used.

The instantaneous classifier 30 is determined in step S30. In the shown embodiment, the instantaneous classifier indicates if a variance Var exceeds a threshold x. The classifier can then be defined as $$\text{artifact}[K_B B] = \begin{cases} 1 & \text{if } \text{Var}[K_B B] > x \\ 0 & \text{otherwise} \end{cases} \quad (15)$$

where artifact=1 means that an artifact is detected and the signal is classified as being 'bad'. The threshold x can be a fixed threshold or an adjustable threshold. Alternatively, the variance Var 29 can directly be used as the instantaneous classifier indicative of a signal quality. However, a threshold decision of step S30 and having a binary classifier 30 is preferred in several application scenarios. For example, a nurse in a general ward or a subject in a home healthcare setting wants clear feedback if the respiration monitor is properly attached. In contrast to the prior art, wherein a quality metric is determined for time windows of for example 30 seconds duration by performing a spectral analysis or determining an entropy feature of the movement signal, the instantaneous classifier thus provides a quality metric with low latency. For example, the variance Var 29 is computed every second.

As an alternative or in addition to the binary decision of step 30, a quality index (QI) 31 can be determined in step S31 based on the variance 29. In this embodiment, a quality index 31 can be determined as $$QI[K_B B] = 100 \cdot \frac{x - \overline{f}[K_B B]}{x}, \quad (16)$$

where $f[K_B B]$ represents a smoothed feature-value. The smoothed feature value can, for example, be given by:

$$\overline{f}[K_B B] = \beta_B \overline{f}[(K_B-1)B] + (1-\beta_B)f[K_B B],$$

with $f[K_BB] \triangleq \text{Var}[K_BB]$ and where $\beta_B$ is a recursive averaging value computed similar to equation (5) by $$\beta_B = \exp\left(-\frac{B}{T_{avg} \cdot F_s}\right), \quad (18)$$

where $F_s$[Hz] is the sampling rate and $T_{avg}$[s] is the averaging time. Exemplary values are B=16, $T_{avg}$=10 seconds and $F_s$=15.625 Hz, giving a value of $\beta_B$=0.9.

Optionally the quality index 31 is presented to the user for evaluating the signal quality. The quality index and/or the instantaneous classifier can be presented visually and/or audibly.

3. Phase Recovery

The previously explained processing for recovering the rotation angle p 26 of block 10 is accurate up to a sign ambiguity. The estimation of the rotation angle p 26 is based on how the gravity-vector is distributed over the three axis of the sensor. Because in practice, the sensor movement depends on factors like posture, physiology and sensor-attachment, the phase of this angular rotation cannot be unambiguously related to a phase of the respiration. Thus no information is provided whether an up-going rotation angle signal p 26 is caused by an inhale or exhale. Furthermore, also the PCA method of step S25 has an inherent sign-ambiguity. A phase recovery block 12 is thus required to distinguish an inhalation phase from an exhalation phase. A respiratory waveform should always be shown with the same orientation, e.g. rising edges of the rotation angle signal correspond to inhalation and falling edges correspond to exhalation, regardless of an orientation of the sensor.

In a first optional step S32 of block 12, the rotation angle signal p 26 is filtered, for example by a low-pass filter (LPF). The output signal of step S32 is a filtered rotation angle signal $p_f$ 32.

Figure 7:
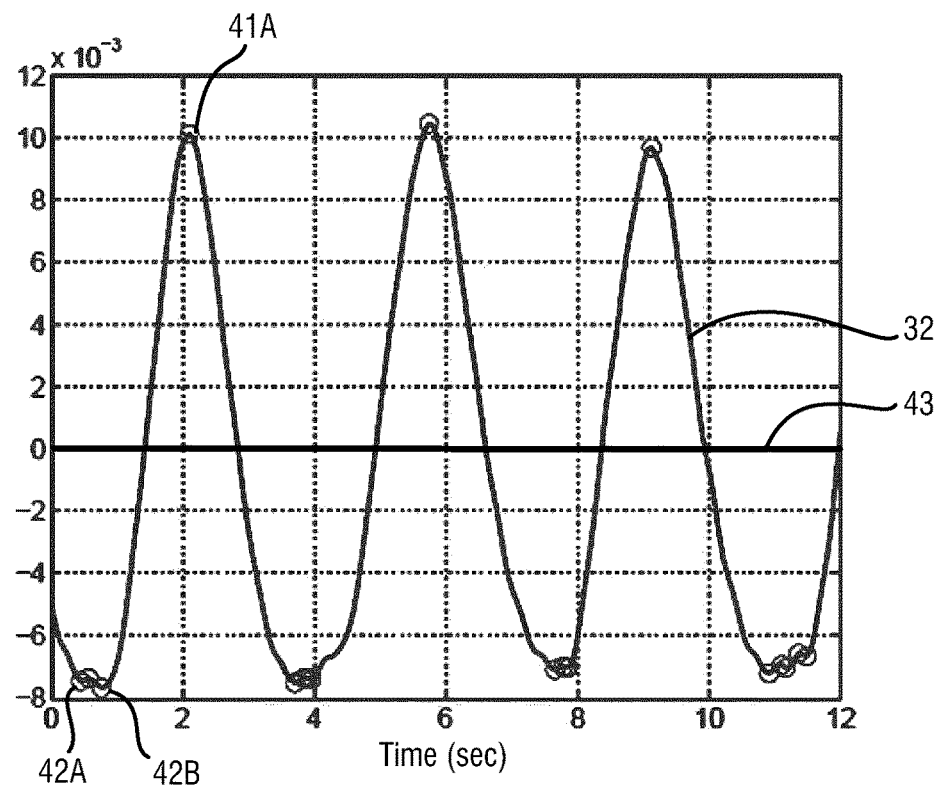
FIG. 7 shows a first graph of a respiration signal.

In a second step S33 of block 12, an orientation of the filtered rotation angle signal $p_f$ 32 is determined. FIG. 7 shows graph of the filtered rotation angle signal $p_f$ as the respiration signal. This filtered rotation angle is analyzed with respect to a baseline curve or baseline level 43. The baseline level 43 splits the waveform into upper and lower part. The baseline 43 can be assumed to be zero. Alternatively, the baseline curve 43 can also be obtained by applying a low-pass filter on the rotation angle with a time-constant spanning several breaths. The graph indicates that there is only a single local extremum 41A during the inhale (above the baseline curve 43) and that there are multiple extrema 42A, 42B during the exhale (below the baseline curve 43). The peak-to-peak rotation angle shown in FIG. 7 is approximately 1 degree. The orientation of the signal 32 is determined by evaluating the number of local extrema of the waveform descriptive of the filtered rotation angle signal 32 which are above the baseline curve and evaluating the number of local extrema of a the same waveform descriptive of the filtered rotation angle signal 32 which are below the baseline curve 43. The waveform is flipped when the number of local extrema above the baseline curve 43 exceeds the number of local extrema below the baseline curve 43. In the example shown in FIG. 7, the waveform has more local extrema below the baseline curve, compared to the number of local extrema above the baseline curve, so there is no need to flip the sign of the signal 32. In the example shown in FIG. 7 a flipping of the waveform can be effected by changing the sign of the signal 32.

To compute the extrema in the filtered rotation angle signal $p_f$[m] 32, two signals representing the gradient of two subsequent samples can be computed as follows:

$$f_1[m] = p_f[m-1] - p_f[m] \quad (19)$$

$$g_2[m] = p_f[m] - p_f[m+1] \quad (20)$$

An extremum for the sample $p_f$[m] is detected e[m] ∈ {0,1} when:

$$e[m] = \begin{cases} 1 & \text{if sgn}\{g_1[m]\} \neq \text{sgn}\{g_2[m]\} \\ 0 & \text{otherwise} \end{cases} \quad (21)$$

To decide when to flip the signal when there are more extrema above the baseline 43 compared to the extrema 43 below the baseline, a cost-measure J[m] can be introduced that counts the net number of the extrema above and below a baseline level. An exemplary cost-measure is given by $$J[m] = \sum_{i=m_0}^{m} e[i] \cdot \text{sgn}\{p_f[i]\}, \quad (22)$$

where $m_0$ is the sample-index from where the cost-measure will be started. This can be e.g. just after a movement artifact has occurred and the patient has possibly changed posture.

Finally, the decision of flipping the sign of the respiratory waveform is done based on this cost-measure J[m], resulting in a phase-compensated respiration angle signal $p^*_f$[m] 33, i.e.:

$$p^*_f[m] = -\text{sgn}\{J[m]\} \cdot p_f \quad (23)$$

An advantage of the proposed phase recovery by integration of the number of extrema is that the more extrema are counted, the less probable it is be that the sign changes during a stable period of breathing.

In a last step S34, the phase-compensated respiration angle signal $p^*_f$ 33 provided by step S33 can be combined with the instantaneous classifier 30 of step S30. The output of step S34 is a respiration signal 34. For example, the phase-compensated respiration angle signal $p^*_f$ 33 is only provided as the output signal 34, if no motion artifact 30 has been detected.

Optionally, also a respiration rate can be determined in step S34, for example by evaluating a temporal peak-to-peak separation in the respiration signal. Based on the time-difference of these peaks, breath-to-breath rates are determined. Finally, multiple breath-to-breath rates are averaged, for example by mean or median computation, the compute an average respiration rate.

Figure 8:
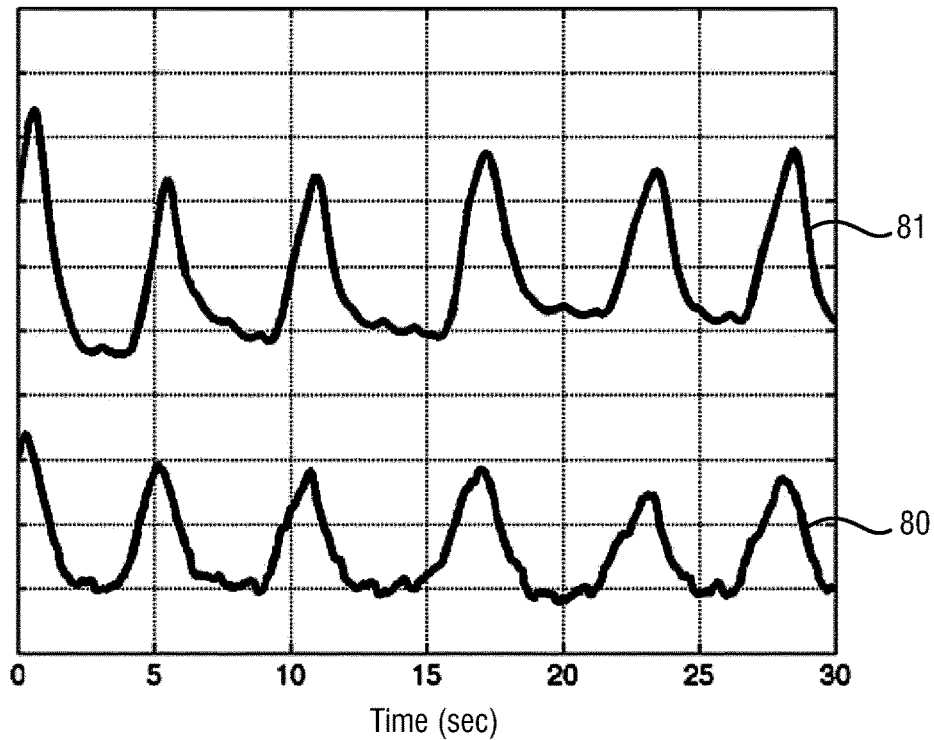
FIG. 8 shows a second graph of a respiration signal.

FIG. 8 shows a graph of two waveforms 80, 81 of two respirations signals of a subject. The first waveform 80 shows a respiration signal obtained using conventional respiratory inductance plethysmography. The second waveform 81 shows a respiration signal determined with the processing apparatus according to an aspect of the present invention. The newly obtained waveform 81 shows good correspondence with the waveform 80 using conventional techniques.

Figure 9A:
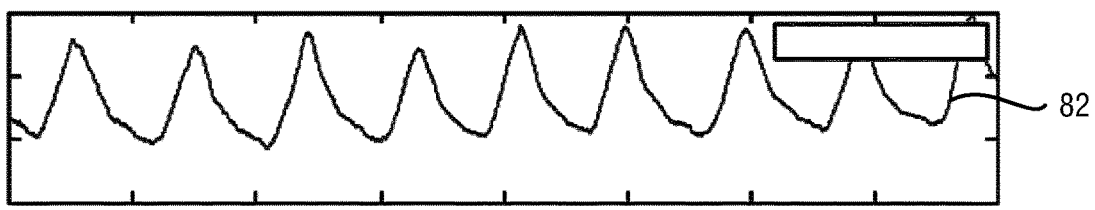
FIG. 9A shows a first exemplary comparison of respiration signals.
Figure 9A:
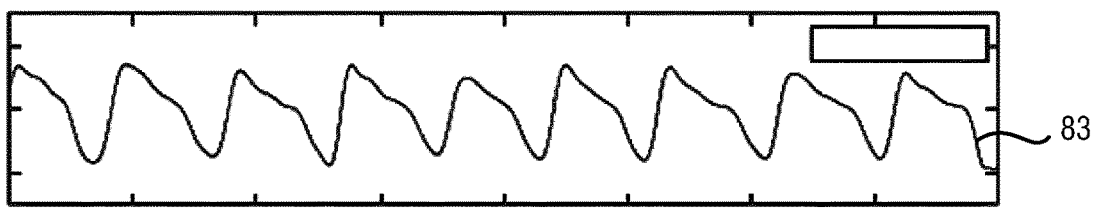
Figure 9A:
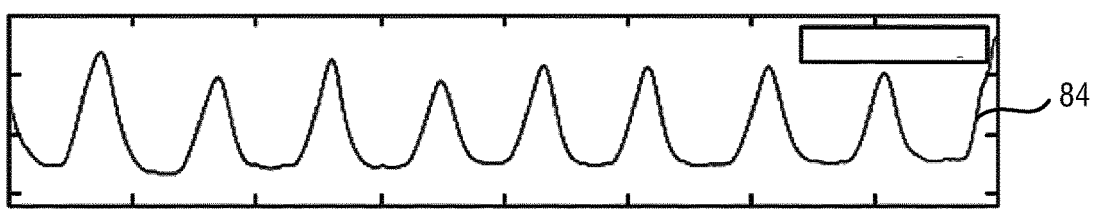
Figure 9B:
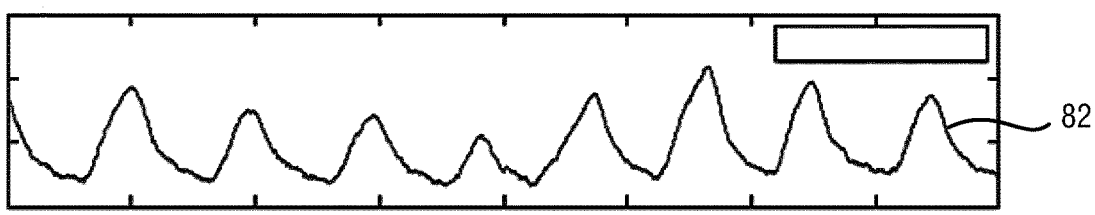
FIG. 9B shows a second exemplary comparison of respiration signals.
Figure 9B:
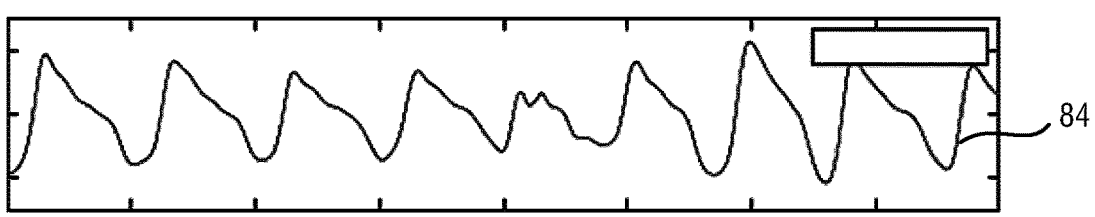
Figure 9B:
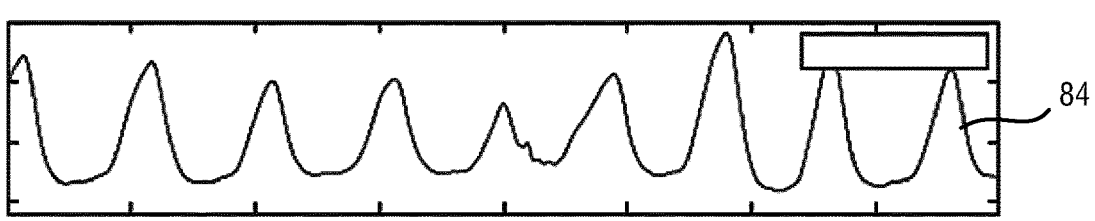

FIGS. 9A and 9B show a comparison of a first waveform 82 obtained using conventional respiratory inductance plethysmography, a second waveform obtained based on the obtained movement signal by applying only an offset removal and PCA but without rotation model, and a third waveform 84 that shows the estimated rotation angle based on the first quantity and the rotation model according to an aspect of the present invention. It can be seen that the second waveform 83 is sufficient for the detection of peaks to compute a respiratory rate. However, the second waveform 83 does not reflect the true chest movement as measured by the waveform 82 with respiratory inductance plethysmography as a reference. The estimated rotation angle that takes into account the rotation model, shown as waveform 84, however, shows a very good resemblance with the reference waveform 82.

FIG. 9B shows an excerpt where the breading rate of the subject 100 is a little bit more irregular in terms of the depth of breathing. Also for this example, the respiration signal 84 determined by the processing apparatus according to an aspect of the present invention shows an improved waveform reconstruction compared to waveform 83.

Figure 10A:
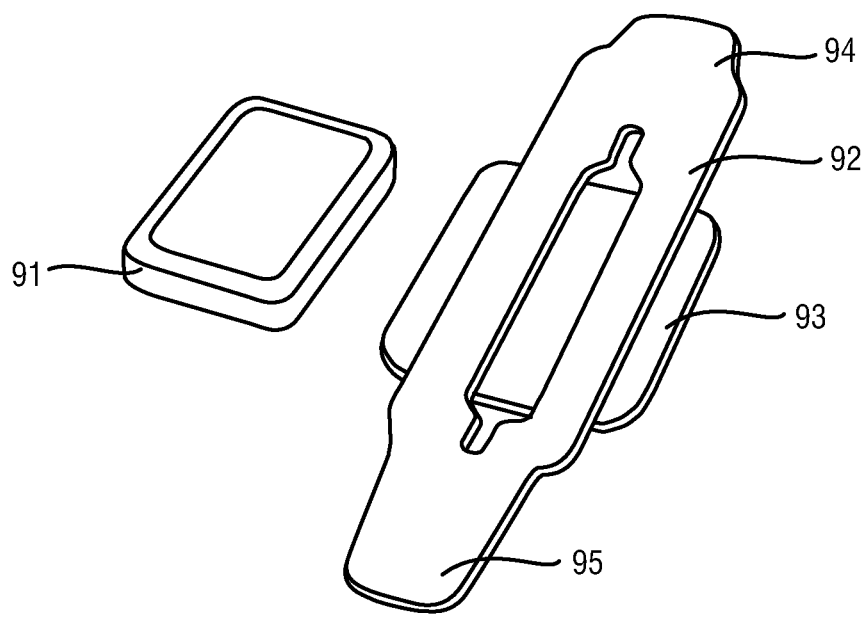
FIGS. 10A and 10B shows a further embodiment of a respiration monitor.
Figure 10B:
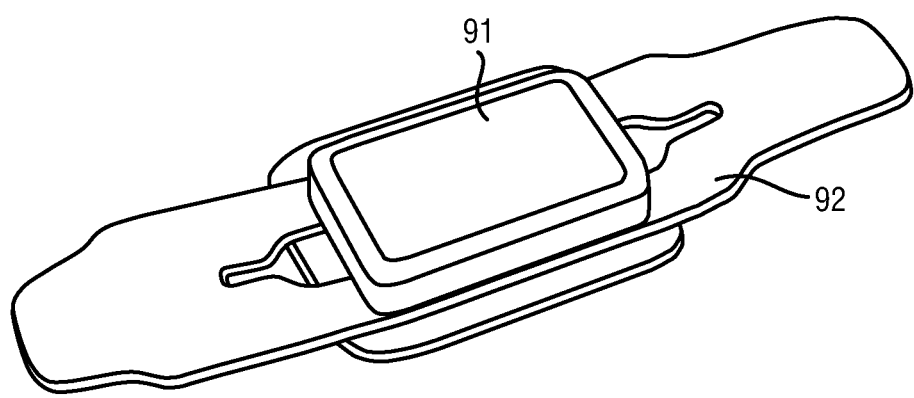

FIGS. 10A and 10B show an alternative embodiment of a respiration monitor 91 according to an aspect of the present invention. In this embodiment, the attachment means 92 comprises a central patch 93 for application to the body of the subject 100, and two flexible wings 94, 95 for embracing the respiration monitor 91 in that the first wing 94 and a second ring 95 can be folded together on top of the respiration monitor 91 for fixation.

In conclusion, the processing apparatus, processing method and respiration monitor presented herein reliably determine a respiration signal. As an advantage, the determination of the respiration signal involves a limited computational effort for low power consumption. Furthermore, a quick initial reading of the respiration signal can be provided along with an instantaneous classifier as a quality metric that is also provided with low latency.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A respiration monitor configured to determine a computed respiration signal of a subject wearing the respiration monitor, the respiration monitor comprising:
   a sensor comprising a multi-axial accelerometer and/or a gyroscope, wherein the sensor obtains a movement signal descriptive of a respiratory movement of the subject;
   a processor configured to:
   (i) receive the obtained movement signal from the sensor;
   (ii) determine a first quantity descriptive of at least one of a rotation axis or a rotation angle based on the obtained movement signal by comparing the obtained movement signal with an averaged movement signal;
   (iii) estimating at least one of the rotation axis or the rotation angle based on the first quantity and a rotation model, wherein the rotation model models the respiratory movement as an anticipated respiratory movement rotating around the estimated rotation axis, wherein the estimated rotation axis is a single, non-averaged rotation axis;
   (iv) determine an estimated movement signal based on the estimated rotation angle, the estimated rotation axis, and the averaged movement signal;
   (v) determine an instantaneous classifier for the obtained movement signal, wherein the instantaneous classifier is descriptive of a mismatch between the obtained movement signal and the estimated movement signal from the rotation model, comprising the steps of:
      (a) calculating a variance between the obtained movement signal and the estimated movement signal; and
      (b) assigning the instantaneous classifier a first value if the calculated variance exceeds a threshold; and
   (vi) generate, using the estimated rotation angle and the instantaneous classifier, the computed respiration signal; and
   an interface configured to communicate the computed respiration signal.

2. The respiration monitor according to claim 1, wherein the step of comparing the obtained movement signal with the averaged movement signal comprises computing a cross product of a vector descriptive of the movement signal and an average vector descriptive of the averaged movement signal.

3. The respiration monitor according to claim 1, wherein the step of comparing the obtained movement signal with the averaged movement signal by the processor comprises accounting for a stability of the respiratory movement.

4. The respiration monitor as claimed in claim 1, wherein the step of estimating at least one of the rotation axis or the rotation angle based on the rotation model comprises the step of performing a principal component analysis of the first quantity.

5. The respiration monitor according to claim 1, wherein the rotation angle is estimated based on a projection of the first quantity onto the estimated rotation axis.

6. The respiration monitor according to claim 1, wherein the processor is further configured to perform the step of:
   recovering a respiratory phase of the respiratory movement.

7. The respiration monitor according to claim 6, wherein the step of recovering the respiratory phase comprises:
   determining the number of local extrema of a waveform descriptive of the estimated rotation angle, and determining a baseline level of the waveform, and
   flipping the waveform when the number of extrema above the baseline level exceeds the number of extrema below the baseline level.

8. A method for determining a computed respiration signal of a subject comprising the steps of:

providing a respiration monitor worn by the subject, the respiration monitor comprising a sensor, a processor, and an interface, wherein the sensor comprises a multi-axial accelerometer;

obtaining, via the multi-axial accelerometer of the sensor, a movement signal descriptive of a respiratory movement of the subject;

determining, by the processor, a first quantity descriptive of at least one of a rotation axis or a rotation angle based on the obtained movement signal by comparing the obtained movement signal with an averaged movement signal;

estimating at least one of the rotation axis or the rotation angle based on the first quantity and a rotation model, wherein the rotation model models the respiratory movement as an anticipated respiratory movement rotating around the estimated rotation axis, wherein the estimated rotation axis is a single, non-averaged rotation axis;

determining an estimated movement signal based on the estimated rotation angle, the estimated rotation axis, and the averaged movement signal;

determining an instantaneous classifier for the obtained movement signal, wherein the instantaneous classifier is descriptive of a mismatch between the obtained movement signal and the estimated movement signal from the rotation model, comprising the steps of:
(a) calculating a variance between the obtained movement signal and the estimated movement signal; and
(b) assigning the instantaneous classifier a first value if the calculated variance exceeds a threshold; and generating, by the processor using the estimated rotation angle and the instantaneous classifier, the computed respiration signal; and communicating the computed respiration signal via the interface.

9. An apparatus for determining a computed respiration signal of a subject, the apparatus configured to be worn by the subject and comprising a sensor, a processor in communication with the sensor, and an interface, wherein the sensor comprises a multi-axial accelerometer, the processor configured to perform the steps of:

obtaining, via the sensor, a movement signal descriptive of a respiratory movement of the subject;

determining a first quantity descriptive of at least one of a rotation axis or a rotation angle based on the obtained movement signal by comparing the obtained movement signal with an averaged movement signal;

estimating, by the processor, at least one of the rotation axis or the rotation angle based on the first quantity and a rotation model, wherein the rotation model models the respiratory movement as an anticipated respiratory movement rotating around the estimated rotation axis, wherein the estimated rotation axis is a single, non-averaged rotation axis;

determining an estimated movement signal based on the estimated rotation angle, the estimated rotation axis, and the averaged movement signal;

determining an instantaneous classifier for the obtained movement signal, wherein the instantaneous classifier is descriptive of a mismatch between the obtained movement signal and the estimated movement signal from the rotation model, comprising the steps of:
(a) calculating a variance between the obtained movement signal and the estimated movement signal; and
(b) assigning the instantaneous classifier a first value if the calculated variance exceeds a threshold; and generating, by the processor using the estimated rotation angle and the instantaneous classifier, the computed respiration signal; and directing the interface to communicate the computed respiration signal.

\* \* \* \* \*